United States Patent
Kazuno et al.

(10) Patent No.: US 8,184,878 B2
(45) Date of Patent: May 22, 2012

(54) IMAGE DIAGNOSIS SUPPORT SYSTEM AND IMAGE DIAGNOSIS SUPPORT METHOD

(75) Inventors: Muneyasu Kazuno, Nasushiobara (JP); Kenichi Niwa, Otawara (JP); Jun Kawakami, Otawara (JP); Koichi Terai, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 938 days.

(21) Appl. No.: 12/107,356

(22) Filed: Apr. 22, 2008

(65) Prior Publication Data

US 2008/0317309 A1    Dec. 25, 2008

(30) Foreign Application Priority Data

Apr. 25, 2007 (JP) ................................ 2007-116124
Mar. 14, 2008 (JP) ................................ 2008-066065

(51) Int. Cl.
*G06K 9/00* (2006.01)
(52) U.S. Cl. ...................... 382/128; 382/131
(58) Field of Classification Search .................. 382/128, 382/131, 154, 160
See application file for complete search history.

(56) References Cited

U.S. PATENT DOCUMENTS

| 7,289,651 | B2 * | 10/2007 | Vining et al. ................ 382/128 |
| 7,346,203 | B2 * | 3/2008 | Turek et al. .................. 382/131 |
| 7,949,166 | B2 * | 5/2011 | Moriya et al. ................ 382/128 |
| 2007/0239489 | A1 | 10/2007 | Masuzawa et al. |

FOREIGN PATENT DOCUMENTS

JP    2007-167634    7/2007

OTHER PUBLICATIONS

U.S. Appl. No. 12/032,266, filed Feb. 15, 2008, Hiroshi Fukatsu et al.
U.S. Appl. No. 12/100,736, filed Apr. 10, 2008, Kenji Matsue et al.
U.S. Appl. No. 12/032,006, filed Feb. 15, 2008, Hiroshi Fukatsu et al.
U.S. Appl. No. 12/100,780, filed Apr. 10, 2008, Muneyasu Kazuno et al.
U.S. Appl. No. 12/260,395, filed Oct. 29, 2008, Futami et al.

* cited by examiner

*Primary Examiner* — Louis Arana
(74) *Attorney, Agent, or Firm* — Oblon, Spivak, McClelland, Maier & Neustadt, L.L.P.

(57) ABSTRACT

Specific information for specifying a specific study or series for which an object, which is obtained by adding at least one information of a scan condition, a scan range, and a key image position as a basis of a diagnosis in an image, is to be generated is specified. It is determined whether or not an image for references is present in the specific study or series on the basis of additional information of at least one image related to the specific study or series. When it is determined that the image for references is present, an object about the specific study or series is generated afterwards, for example, in the unit of series by using the image for references and at least one information of a scan condition, a scan range, and a key image position of the additional information.

16 Claims, 11 Drawing Sheets

FIG. 5

| INFORMATION NAME | IDENTIFIER | ACQUISITION PLACE (STORAGE PLACE) | TYPE | TABLE | COLUMN |
|---|---|---|---|---|---|
| SERIES UID | 0020, 002e | IMAGE STORAGE UNIT | DB | View-Image | SeriesUID |
| IMAGE TYPE | 0008, 0008 | IMAGE STORAGE UNIT | IMAGE | | |
| IMAGE LOCATION | 0020, 0032 | IMAGE STORAGE UNIT | IMAGE | | |
| REPORT UID | 0020, 0099 | REPORT STORAGE UNIT | REPORT | | |
| ... | | | | | |

FIG. 10

| ITEM | ADDITION WEIGHT |
|---|---|
| TUBE VOLTAGE | 5 |
| TUBE CURRENT | 5 |
| RECONSTRUCTION FUNCTION | 4 |
| . . . | |

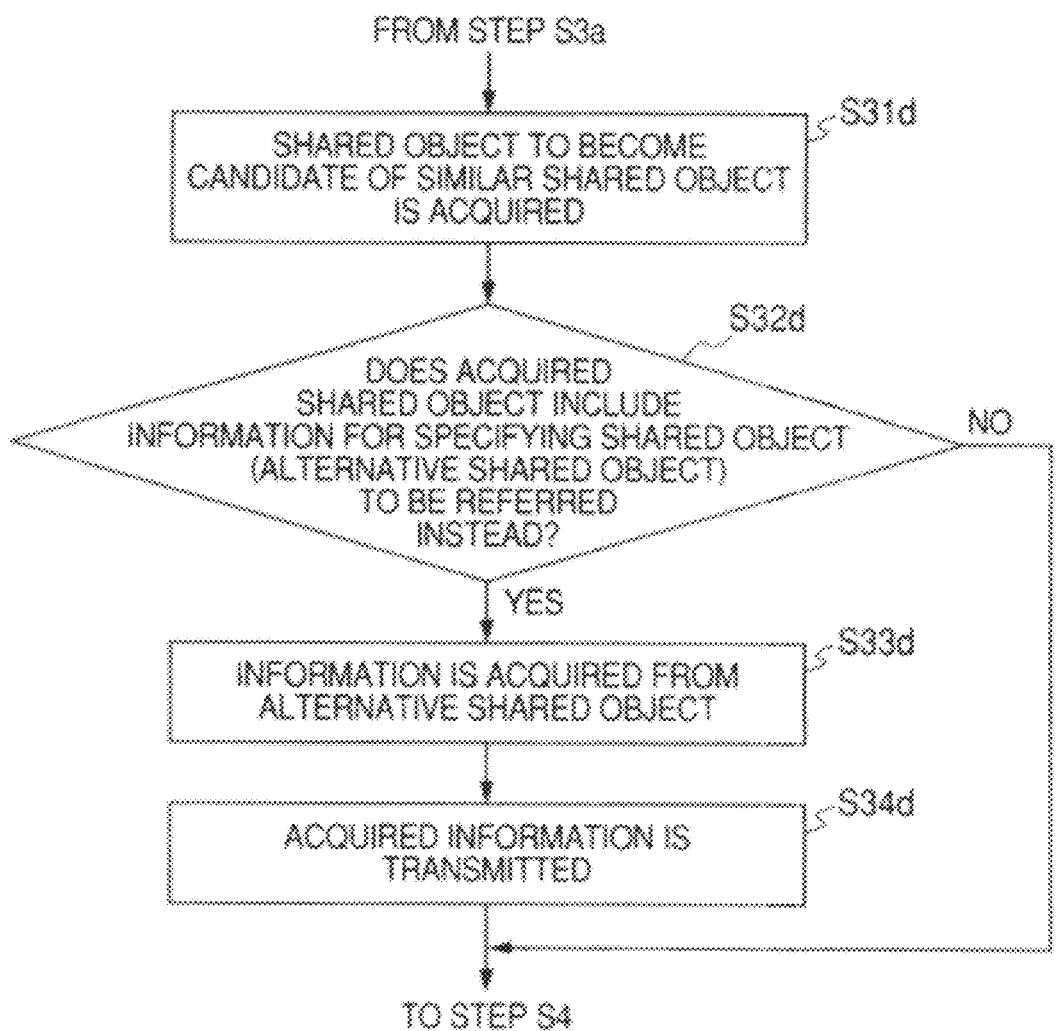

IMAGE DIAGNOSIS SUPPORT SYSTEM AND IMAGE DIAGNOSIS SUPPORT METHOD

CROSS-REFERENCE TO RELATED APPLICATIONS

This application is based upon and claims the benefit of priority from prior Japanese Patent Applications No. 2007-116124, filed Apr. 25, 2007; and No. 2008-066065, filed Mar. 14, 2008, the entire contents of both of which are incorporated herein by reference.

BACKGROUND OF THE INVENTION

1. Field of the Invention

The present invention relates to an image diagnosis support system and an image diagnosis support method for generating a shared object, which has information (scan information) set in past scan, information on an image (key image) used as a basis in a diagnosis, and information on a past study referred at the time of scan as contents thereof, afterwards and managing the shared object in a study executed by using a medical image diagnostic apparatus.

2. Description of the Related Art

In recent years, specialized fields of medical practice are subdivided. For example, a work in image diagnosis is divided into acquisition of a diagnostic image of a patient, image interpretation of an acquired diagnostic image and report preparation, explanation of treatment courses or a diagnostic result based on a report result, and the like. Each expert (doctor in charge or technician in charge) takes charge of each work and the medical practice, such as a diagnosis, for a patient, is attained by all of the works. Each expert executes each work on the basis of information that the other experts created in preceding works while appropriately referring to past diagnostic information and the like. For example, these works are performed in a medical image diagnostic apparatus for acquiring a diagnostic image, such as an X-ray CT apparatus or an MRI apparatus, a PACS server that stores a diagnostic image, an image reference apparatus for interpreting a diagnostic image, an image diagnosis report preparation support apparatus, and the like.

In recent years, a system that makes it possible to efficiently use specific information on a past study at the time of an image diagnosis, in which such works are subdivided, is proposed (for example, refer to Jpn. Pat. Appln. KOKAI Publication No. 2007-167634. This means that an object, which has information used in past scan, information on a key image, and information on a past study referred at the time of scan as contents thereof, are shared as information. A user may check a key image or a scan condition used in the past diagnosis by referring to the shared object at arbitrary timing in an arbitrary apparatus. For example, the user may reproduce a past study with high precision and obtain an image suitable for comparison interpretation. In addition, in the case of a study scanned with reference to past information, reference history thereof is also stored in a shared object. Accordingly, at the time of image interpretation, a comparison object to be referred may be automatically specified from the information and be displayed. As a result, preparation for image interpretation of a doctor, who performs image interpretation, is significantly reduced.

However, in the case of a study already performed before the system that uses a shared object is introduced, a shared object is not stored. Accordingly, a user should perform the same work as before the system is introduced. For this reason, the following problems are present in the work, for example.

In the case of scan a study suitable for comparison interpretation with respect to previous scan, a technician needs to perform a scan work while referring to and checking an interpretation report of the previous study. As a result, the precision and the study efficiency decrease. Furthermore, at the time of image interpretation, since a preparatory work before starting comparison interpretation, such as selection of a key image and setting of image parameters, is needed, the efficiency of image interpretation is lowered. These problems are noticeable particularly in a large hospital that spends most of the daily studies for comparison with a past study, such as check of a progress. Therefore, it is in urgent need to allow a shared object to be also used in a study in which scan was already completed.

SUMMARY OF THE INVENTION

It is an object of the invention to provide an image diagnosis support system and an image diagnosis support method capable of generating a shared object afterwards even for a study or series executed before a system that uses a shared object is introduced.

According to a first aspect of the invention, an image diagnosis support system includes: a specifying unit that specifies specific information for specifying a specific study or series for which an object, which is obtained by adding at least one information of a scan condition, a scan range, and a key image position as a basis of a diagnosis in an image, is to be generated; a first determination unit that determines whether or not an image for references is present in the specific study or series on the basis of additional information of at least one image related to the specific study or series; and a first generation unit that generates the object by using the image for references and at least one information of a scan condition, a scan range, and a key image position of the additional information when it is determined that the image for references is present.

According to a second aspect of the invention, an image diagnosis support system includes: a specifying unit that specifies specific information for specifying a medical imaging including a plurality of images; a first determination unit that determines whether or not an image for references related to the medical image specified by the specified specific information is present; and a generation unit that generates an object by using the image for references and information, which includes at least one of a scan condition, a scan range, and a position of a key image used as a basis of a diagnosis, of additional information of the medical image specified by the specific information when it is determined that the image for references is present.

According to a third aspect of the invention, an image diagnosis support system includes: a specifying unit that specifies specific information for specifying a specific study or series for which an object, which is obtained by adding at least one information of a scan condition, a scan range, and a key image position as a basis of a diagnosis in an image, is to be generated; an acquisition unit that acquires a report related to the specific study or series; a determination unit that determines whether or not link information, which indicates a storage place of an image related to other studies or series different from the specific study or series, is included in the acquired report; and a generation unit that generates the object by using information, which is extracted from the link information and specifies an image related to the other studies or series, and at least one information of a scan condition, a scan range, and a key image position of additional information of at least one image related to the specific study or series when it is determined that the link information is present.

According to a fourth aspect of the invention, an image diagnosis support method includes: specifying a specific study or series for which an object, which is obtained by adding at least one information of a scan condition, a scan range, and a key image position as a basis of a diagnosis in an image, is to be generated; determining whether or not an image for references is present in the specific study or series on the basis of additional information of at least one image related to the specified specific study or series; and generating the object by using the image for references and at least one information of a scan condition, a scan range, and a key image position of the additional information when it is determined that the image for references is present.

According to a fifth aspect of the invention, an image diagnosis support method includes: specifying specific information for specifying a medical image including a plurality of images; determining whether or not an image for references related to the medical image specified by the specified specific information is present; and generating an object by using the image for references and information, which includes at least one of a scan condition, a scan range, and a position of a key image used as a basis of a diagnosis, of additional information of the medical image specified by the specific information when it is determined that the image for references is present.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5 is a view illustrating an example of a storage place table used in processing for acquiring/analyzing related information shown in FIG. 3;

FIG. 10 is a view illustrating an example of a similarity decision table used in the processing for using a similar shared object shown in FIG. 9; and FIG. 11 is a flow chart illustrating processing for using an alternative shared object in a third embodiment of the invention, which is executed in step S3b of FIG. 8.

DESCRIPTION OF THE PREFERRED EMBODIMENTS

Figure 1:
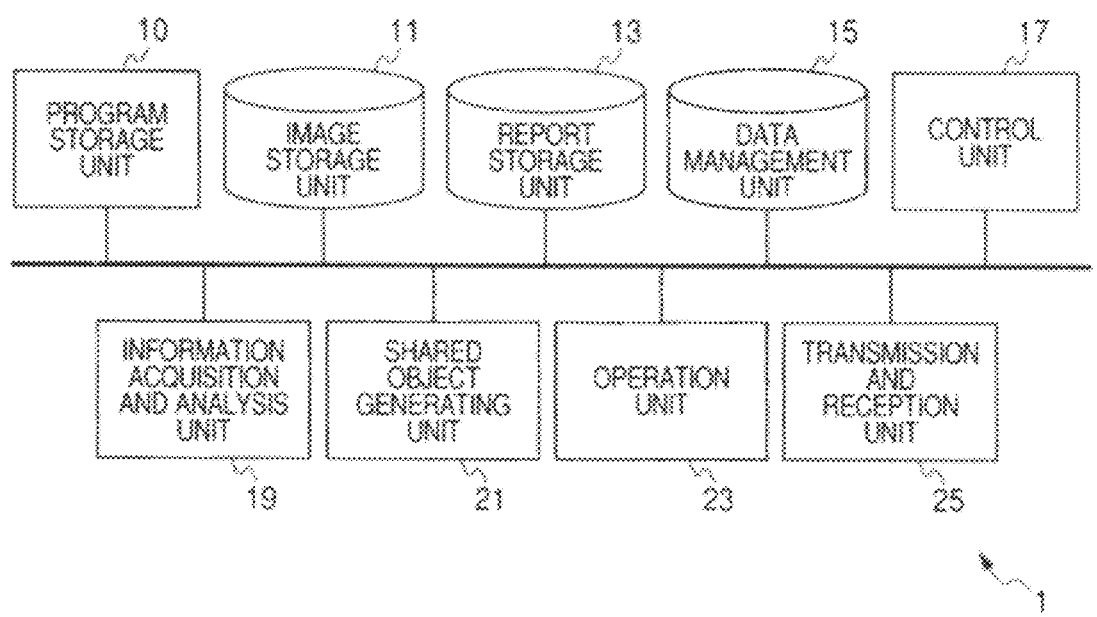
FIG. 1 is a block diagram illustrating the configuration of a medical image storage apparatus according to first to third embodiments of the invention.

Hereinafter, an image diagnosis support system and an image diagnosis support method according to first to third embodiments of the invention will be described with reference to the accompanying drawings. Moreover, in the following description, components having approximately the same function and configuration are denoted by the same reference numeral, and repeat of explanation will only be made as needed.

Furthermore, in the following description, a case in which image diagnosis support systems according to the first, second, and third embodiments of the invention are realized by causing a medical image storage apparatus to have an image diagnosis support function, which will be described later, will be explained. However, the invention is not limited to the above case. For example, the image diagnosis support systems according to the first, second, and third embodiments of the invention may be realized by providing the image diagnosis support function in other apparatuses, such as a report preparation support apparatus, a medical image observation apparatus, and a medical image diagnostic apparatus (computerized X-ray tomographic apparatus (X-ray CT apparatus) or a magnetic resonance imaging apparatus, an ultrasonic diagnostic apparatus, a nuclear medicine diagnostic apparatus, an X-ray diagnostic apparatus, and the like).

First Embodiment

FIG. 1 is a block diagram illustrating the configuration of a medical image storage apparatus 1 according to a first embodiment. As shown in FIG. 1, the medical image storage apparatus 1 includes a program storage unit 10, an image storage unit 11, a report storage unit 13, a data management unit 15, a control unit 17, an information acquisition and analysis unit 19, a shared object generating unit 21, an operation unit 23, and a transmission and reception unit 25.

The program storage unit 10 stores various kinds of programs, such as a dedicated program for realizing an image diagnosis support function to be described later and a program for reproducing a shared object.

The image storage unit 11 stores various medical images acquired by the medical image diagnostic apparatus.

A medical image is based on DICOM standard, for example. Medical images are managed for every study or every series as needed.

The report storage unit 13 stores a report created by using the report preparation support apparatus. A report is created for an image (key image) belonging to a predetermined study. A user summarizes an opinion about a current study in a report by performing comparison reading of a current image, which has been scanned in the current study to be reported, and a past image obtained in a past study. The report includes the opinion as character information. Furthermore, the report usually includes link information that specifies a storage place of the past image to be compared. For example, link information may be included in a specific character string included in the opinion. Thus, the past image and the specific character string in which the link information is included are related (hyperlinked) to each other. A past image of a linked place is displayed on a screen by selecting the character string, in which the link information is included, on the screen. The link information is address information indicating an image storage place within the image storage unit 11, for example.

The data management unit 15 stores a storage place table, in which each storage place of a DICOM object acquired in each study is defined, and manages updating of the contents and the like. The DICOM object is an image, additional information, a shared object, a report, and the like based on DICOM standard. In addition, the data management unit 15 stores a similarity determination table for determining the similarity between studies and manages updating of the contents and the like.

The control unit 17 makes an overall control of a static or dynamic operation of the medical image storage apparatus 1. In addition, the control unit 17 realizes an image diagnosis support function, which will be described later, by loading a dedicated program into a memory (not shown).

The information acquisition and analysis unit 19 acquires various kinds of information required to generate a shared object afterwards by using the storage place table stored in the data management unit 15. In addition, the information acquisition and analysis unit 19 analyzes the acquired various kinds of information and specifies information serving as additional information of a shared object. In addition, the information acquisition and analysis unit 19 analyzes the acquired various kinds of information and determines whether or not an image for generating a reference image of the shared object is present. The reference image is an image for indicating at least one of the scan range in a study or series and the key image position as a basis in a diagnosis. Hereinafter, an image for generating a reference image is assumed to be called an image for references. In the case when the image for references is not present, the information acquisition and analysis unit 19 analyzes acquired various kinds of information and generates an image for references from a scan-completed image as necessary.

Series is an index for managing information and serves to classify information by using a time (when was information generated?), a space (where was information generated?), and a clinical characteristic (which kind of clinical meaning is included?) of information as signs. An image acquired in one study is generally classified and managed by a plurality of series. A Series UID and a study UID (study UID) are managed so as to be related to each other. In addition, among a plurality of series belonging to the same study, reference images may be different while a reference image may be common (the same).

The shared object generating unit 21 generates a shared object, which includes image information and additional information, according to an image diagnosis support function to be described later. The shared object is generated to effectively use information used at the time of medical practice, such as information on a reference image or a scan position, a scan range, a scan condition, an image generation condition, and a key image, information on a report, and link information. The shared object will be described in detail later.

The operation unit 23 includes a keyboard, various switches, a mouse, a button (for example, a GUI), and the like and is a device capable of inputting an instruction from an operator. In addition, the operation unit 23 includes a dedicated I/F used to instruct execution of image diagnosis support processing to be described later.

The transmission and reception unit 25 receives/transmits an image or a shared object, execution data of a report, or various kinds of information required to generate a shared object from/to another apparatus through a network.

In addition, in the first embodiment, the medical image storage apparatus 1 is configured to include the image storage unit 11 and the report storage unit 13. However, the image storage unit 11 or the report storage unit 13 may also be provided in another apparatus on a network through which transmission/reception of information to/from the medical image storage apparatus 1 is possible without being limited to the above case.

(Shared Object)

Figure 2:
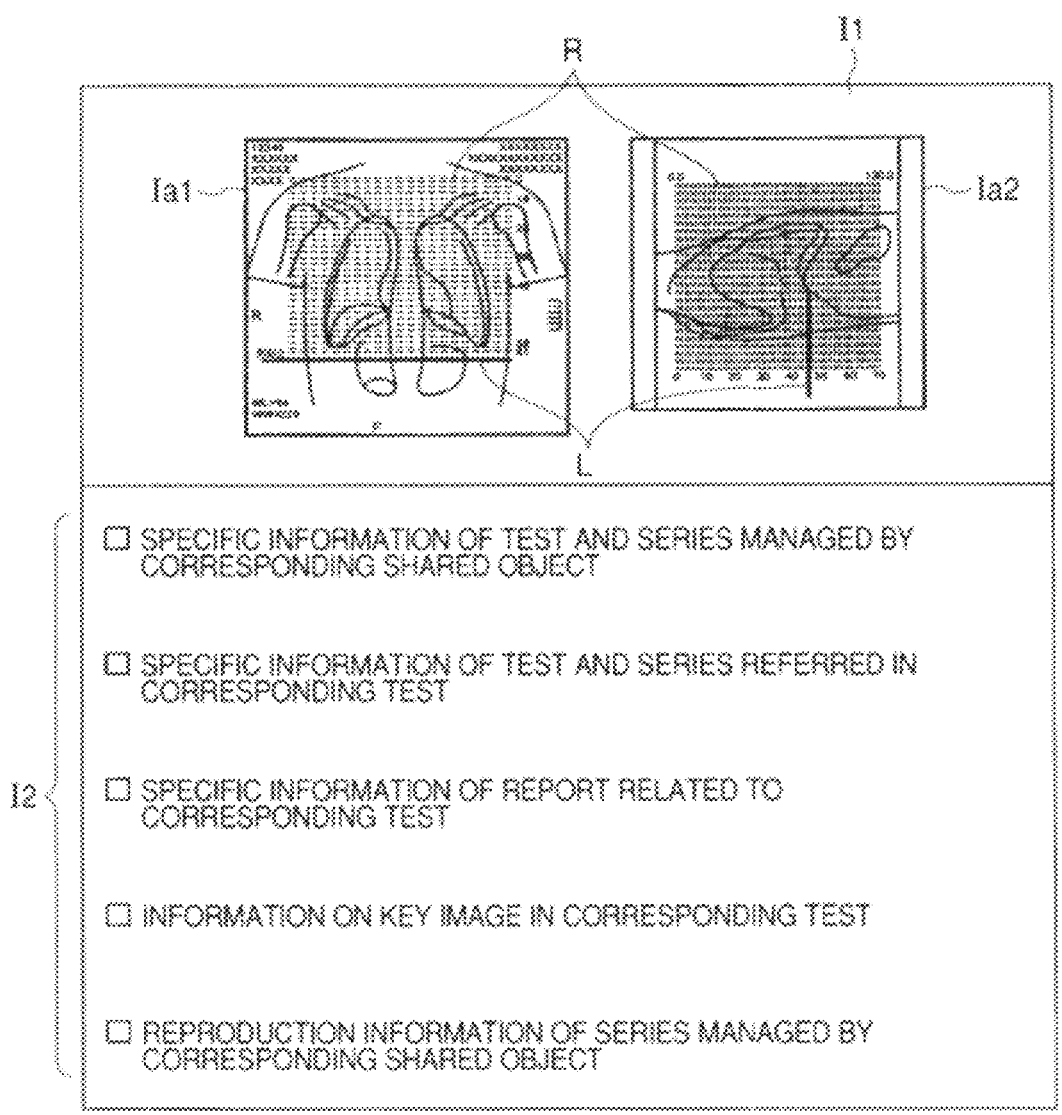
FIG. 2 is a view for explaining the configuration of a shared object generated by a shared object generating unit shown in FIG. 1.

Next, a shared object will be described. FIG. 2 is a view illustrating the configuration of a shared object. A shared object includes image information I1 and additional information I2, as shown in FIG. 2, for example. The shared object is generated and managed as an image based on the DICOM standard, for example, for every study or every series.

[Image Information]

As shown in FIG. 2, the image information I1 has one or a plurality of reference images Ia1 and Ia2 on which a range R or the position is shown. For example, the reference image Ia1 and Ia2 are scanograms used in an X-ray CT apparatus or coronary images generated by pilot scan in an MRI apparatus. The reference image may also be called a 'scout image' or 'Localizer'. The range R is a physical range where a medical image diagnostic apparatus actually supplies energy by using an X ray or a high frequency and a detector detects a signal or generates an image on the basis of the supplied energy. For example, in the case of the X-ray CT apparatus 1, the range R is a range in the body axis direction reconstructed on the basis of projection data detected by the detector, that is, a reconstruction range. In addition, in the case of an MRI apparatus, the range R is a scan range. In general, the range R may be expressed by a dotted line or the like on reference images Ia1 and Ia2 acquired before scan and may be shown together with a line indicating an image generation pitch in the body axis direction. Moreover, in the case of the image information I1, a marker L indicating the key image position may be drawn on the reference images Ia1 and Ia2 or the key image (actual data of the key image) itself may be drawn if necessary.

In addition, when editing processing is admitted in the image diagnosis support function to be described later, actual data of a key image managed as corresponding image information, key image positions L on the reference images Ia1 and Ia2, and the like are edited according to an editing instruction received from the medical report preparation support system.

[Additional Information]

As shown in FIG. 2, the additional information I2 may be largely classified into five kinds of information of specific information of study and series corresponding to a corresponding shared object, specific information of study and series referred in a corresponding study, specific information of a report related to a study corresponding to a corresponding shared object, information on a key image of a study corresponding to a corresponding shared object, and reproduction information of study and series corresponding to a corresponding shared object. Hereinafter, each of the information will be described.

[Additional Information 1: Specific Information of Study and Series Corresponding to a Corresponding Shared Object]

This additional information is information for distinguishing a corresponding shared object from other shared objects. The additional information includes an identifier (object UID) of the corresponding (shared) object, a managed series identifier (managed series UID), and a managed study identifier (managed study UID).

The object UID is information for distinguishing (specifying) the corresponding object from other objects. The object UID is numbered by an object generating unit of each apparatus so as not to overlap when a shared object is generated. The managed series UID is information for specifying series to be managed through a corresponding shared object. The managed study UID is information for specifying a study to be managed through a corresponding shared object.

[Additional Information 2: Specific Information of Study and Series Referred in a Corresponding Study]

This additional information is information indicating the relationships between the corresponding shared object and other shared objects. The additional information includes a parent (shared) object identifier (parent object UID), a related series identifier (related series UID), a corresponding series UID, and a related study identifier.

The parent object UID is information for specifying an object (parent object) referred to generate a corresponding object. The related series UID is information for specifying series using the same condition (for example, a scan condition and a reference image) as the corresponding shared object. A plurality of related series UIDs may be present in unique information on an object. The corresponding series UID is information for specifying series in which a scan condition and the like are indicated by the corresponding shared object.

In addition, data specified by UIDs is linked. Accordingly, it becomes possible to quickly trace the derived study progress of an image group by accessing data of a linked place on the basis of each UID. In addition, a creation date or a creation time of a shared object may be included in unique information of an object.

[Additional Information 3: Specific Information of a Report Related to a Study Corresponding to a Corresponding Shared Object]

This additional information is an identifier (report identifier) for specifying a report generated in a corresponding study. In addition, a report that was created may be modified later or a new report may be additionally generated for a predetermined study. When different identifiers are numbered for the reports, all report identifiers or report identifiers selected according to a predetermined condition are assumed to be included.

[Additional Information 4: Specific Information on a Key Image of a Study Corresponding to a Corresponding Shared Object]

This additional information is information (for example, an SOP instance UID based on the DICOM standard) for specifying a key image used in interpretation or image diagnosis performed by a component of the medical image storage apparatus 1 and information for specifying actual data of a key image and the position or direction of the key image (for example, z-axis coordinate position, direction at the time of observation, enlargement ratio, and information called WW/WL). Moreover, in the case when a key image is an MPR image, the position or direction, a generation condition, and the like related to the MPR image serving as a key image may be included in corresponding additional information in the same manner as an image generation condition.

In the image diagnosis support processing to be described later, it is determined whether or not editing processing can be performed or the type of editing processing is determined according to a report creator and the combination of an apparatus used for the report preparation, and corresponding additional information is managed according to a result of the determination.

[Additional Information 5: Reproduction Information of Study and Series Corresponding to a Corresponding Shared Object]

This additional information is information for reproducing processing executed in a past study or series. The additional information includes a scan condition, an image generation condition, and the like.

The scan condition is a physical condition required for collecting physical data, which is a source of image generation, from a patient by a scan operation. Content of the condition depends on the type of modality. For example, scan conditions of the X-ray CT apparatus include the start position of scan, a scan range (bed movement amount), KV/mA of an X-ray tube, and a beam pitch. In addition, the beam pitch is the bed movement amount while the X-ray tube rotates once with respect to the total width of an obtained image slice.

However, the content of the scan conditions is not limited to the example. For example, the scan conditions may include the direction (information on whether legs are first inserted or a head is first inserted into the apparatus) in which a patient is inserted at the time of a study, information on whether or not a contrast agent is to be injected, an amount of the contrast injected, the type of medicine, patient's posture (direction and posture in which a patient is laid on a bed), and the like. In order to reduce the amount of exposure, there is a function of automatically controlling KV/mA so as to obtain a constant image quality. In this case, however, an image noise (SD value) that is a control amount may be included in a scan condition.

In addition, scan conditions of an MRI apparatus include a scan range, the direction or posture in which a patient is inserted, the magnetic field intensity, a pulse sequence, the type of a detection coil, a place where a detection coil is provided, electrocardiographic synchronization, and respiratory synchronization, bed ventilation, a body portion focused at the time of scan, and a fixing position.

The image generation condition is a parameter for reconstructing an image from the physical data obtained by scan. For example, the image generation conditions include filter processing parameters, such as a reconstruction range or time phase, the position, direction thickness, FOV (enlargement ratio), and a reconstruction function. In addition, the image generation conditions include conditions used in image processing, such as volume rendering or MPR processing, executed in various medical image diagnostic apparatuses or image reference apparatuses. For example, in the case of MPR processing, reference coordinates, a normal vector, the slice thickness, a range, and the like are included.

In addition, the reconstruction range may be defined by a reference image in which the reconstruction range is shown. In this case, one shared object has a plurality of reference images in which a plurality of reconstruction ranges are shown.

An image that can be compared with a previous image at the start of a study can be scanned properly and thoroughly by causing a shared object to have the additional information described above. In addition, the shared object does not need to have all of the information described above, but the content of a shared object may be changed according to a used apparatus or the purpose as long as information used when executing medical practice can be effectively used. For example, additional information in a shared object used in a medical image diagnostic apparatus may include a patient ID, positional information on a scan range (reconstruction range), and a landmark. For example, additional information in a shared object used in a PACS may include a patient ID and positional information and landmark of a key image. In addition, in the case when a reference image is not needed and only a past scan condition is required, a shared object may be configured to have only additional information including a scan condition and the like.

(Image Diagnosis Support Function)

Next, an image diagnosis support function in the first embodiment will be described. This function is to generate a shared object afterward and to manage the shared object in a study executed before a system using the shared object is introduced.

Figure 3:
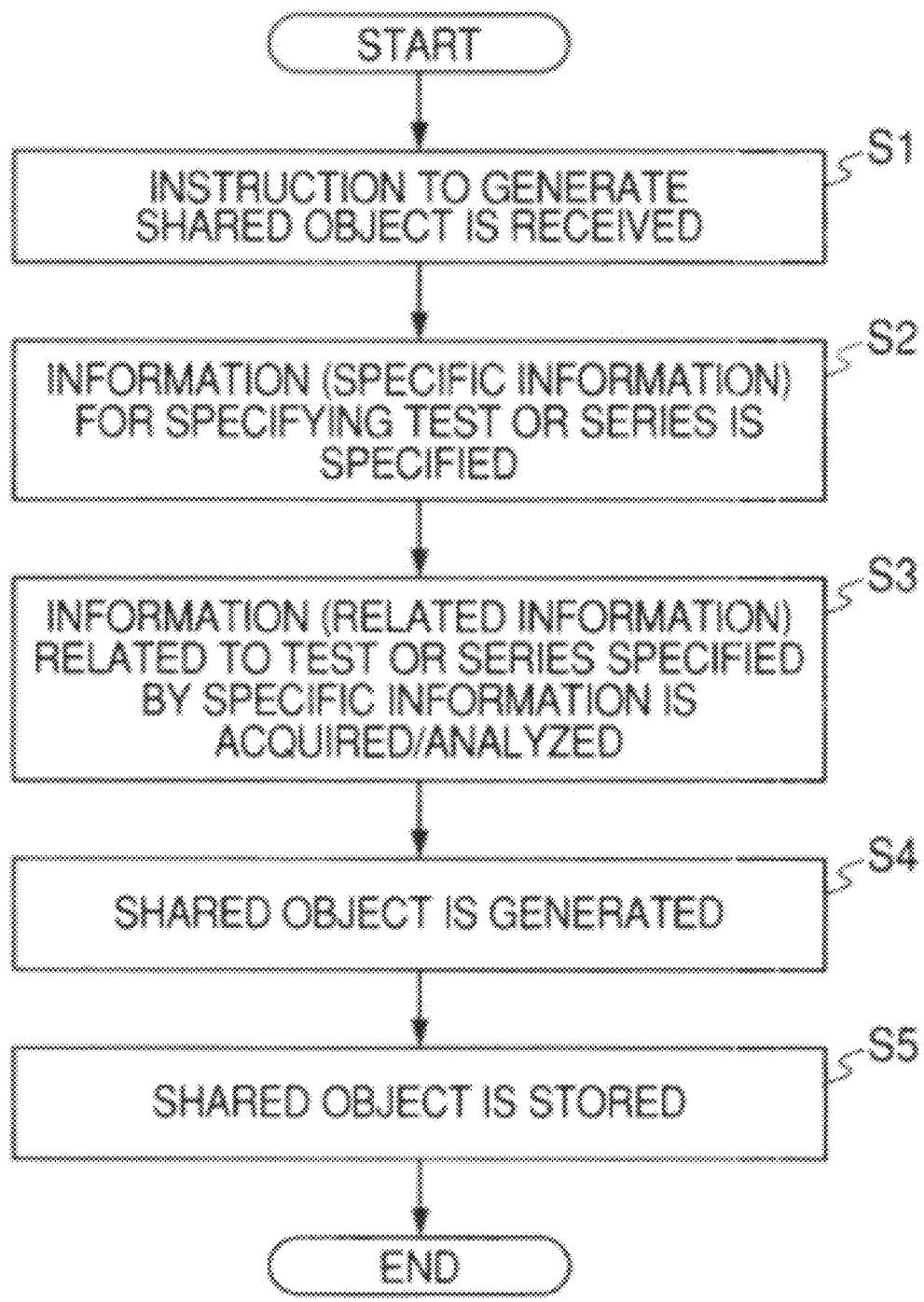
FIG. 3 is a flow chart illustrating image diagnosis support processing in the first embodiment, which is executed under the control of a control unit shown in FIG. 1.

FIG. 3 is a flow chart illustrating processing (image diagnosis support processing), which is executed under the control of the control unit 17, according to the image diagnosis support function in the first embodiment. As shown in FIG. 3, the image diagnosis support processing may be largely classified into processing for receiving an instruction to generate a shared object (step S1), processing for acquiring specific information of a study or series (step S2), processing for acquiring/analyzing related information of a study or series (step S3), processing for generating a shared object (step S4), and processing for storing a shared object (step S5). Hereinafter, each of the steps will be described.

[Reception of an Instruction to Generate a Shared Object: Step S1]

First, the control unit 17 receives an instruction to generate a shared object by user's predetermined input through the operation unit 23 (step S1).

[Specification of Information (Specific Information) for Specifying a Study or Series: Step S2]

When the generation instruction is received, the control unit 17 makes the information acquisition and analysis unit 19 specify specific information of a study or series for which a shared object is to be generated afterwards (step S2). As an example of the specific information, a study instance ID, a series UID, a patient ID, a study UID, and time information on the study, such as a study date or a study time, may be mentioned, for example. In addition, a user may input specific information through the operation unit 23 when receiving the generation instruction in step S1.

[Acquisition/Analysis of Information (Related Information) Related to a Study or Series Specified by Specific Information: Step S3]

The processing for acquiring/analyzing related information is largely divided into processing A for acquiring related information, processing B for acquiring information that specifies an image for references, and processing C for acquiring the specific information of a past study or series relating to the study. The processing A and the processing B will be first described together and then the processing C will be described.

<Processing A for Acquiring Related Information and Processing B for Acquiring Information that Specifies an Image for References>

Figure 4:
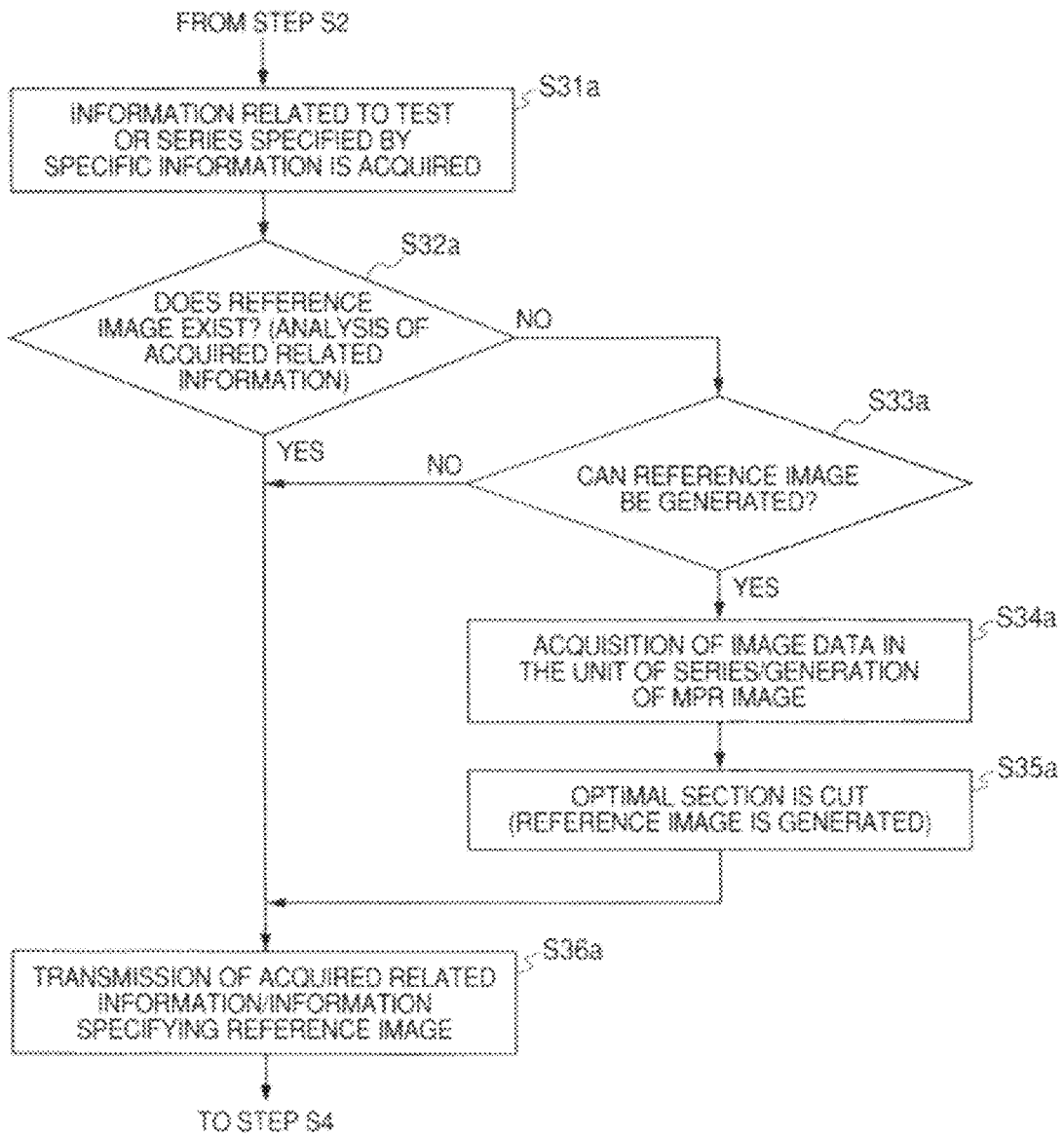
FIG. 4 is a flow chart illustrating processing for acquiring/analyzing related information executed in step S3 shown in FIG. 3.

FIG. 4 is a flow chart illustrating the flow of processing (processing A & processing B) for acquiring/analyzing related information that is executed by the information acquisition and analysis unit 19 in step S3. As shown in FIG. 4, the information acquisition and analysis unit 19 accesses a storage place defined in a storage place table within the data management unit 15 by using the specific information specified in step S2 and acquires related information (step S31a).

FIG. 5 is a view illustrating an example of the storage place table stored in the data management unit 15. For example, in the case of acquiring a UID of series related to a study or series specified by specific information, the information acquisition and analysis unit 19 accesses the image storage unit 11, which is a storage place (acquisition place), by referring the storage place table and acquires series UID, which is managed as '0020, 002e', as related information. Similarly, the information acquisition and analysis unit 19 acquires, as the related information, information (for example, a series instance UID) for specifying the configuration of a study or series specified by related information, DICOM additional information (for example, image position, image direction, an image type, a scan range, a tube voltage, a tube current, and an image generation parameter) including a scan condition or an image generation condition, and information for specifying a key image by using a storage place table.

When the related information is acquired, the information acquisition and analysis unit 19 analyzes the acquired related information and determines whether or not an image for references is present in the image acquired in the past (step S32a). That is, the information acquisition and analysis unit 19 classifies the related information for every series on the basis of the series instance UID, analyzes the image type, the image position, the image direction, and the like of each image for every series, and determines whether or not the image for references is present in the study or series.

In general, the image position or the image direction of a reference image is different from that of an image that is not a reference image. In the case of scan using a CT or an MR, a reference image is a sagittal section or a coronary section, for example. However, other plural images are axial sections in many cases.

Then, when the image direction or the image position of the plurality of images included in series of CT scan is analyzed and an image indicating a sagittal section or a coronary section can be specified, the information acquisition and analysis unit 19 determines that an image for references is present in the study or series. Furthermore, for example, in the case when the image type indicating the image for references is specified, the information acquisition and analysis unit 19 determines that the image for references is present in the study or series.

When it is determined that an image for references is not present (step S32a: NO), the information acquisition and analysis unit 19 executes processing for generating the image for references.

In the processing for generating an image for references, the information acquisition and analysis unit 19 analyzes the image position, the image direction, the image type, a scan range, and the like for every series from the acquired related information and determines whether or not the reference image can be generated (step S33a). When it is determined that the reference image can be generated (step S33a: YES), the information acquisition and analysis unit 19 acquires actual data of an image in the unit of series and generates an MPR image using the actual data of the acquired image (step S34a). Then, the information acquisition and analysis unit 19 generates the image for references by cutting an optimal section (that is, an optimal MPR image) for the image for references from the generated MPR image on the basis of information, such as the image position or the image direction, of each image data in the unit of the acquired series (step S35a). The generated image for references is stored in the image storage unit 11. In addition, a storage place of the image for references is registered in a storage place table included in the data management unit 15. After step S35a ends, the information acquisition and analysis unit 19 proceeds to step S36a.

When it is determined that an image for references cannot be generated in step S33a (step S33a: NO), the information acquisition and analysis unit 19 proceeds to step S36a.

When it is determined that an image for references is present in step S32a (step S32a: YES), the information acquisition and analysis unit 19 proceeds to step S33a.

When it is determined that an image for references is present in step S32a or when an image for references was generated in step S35a, the information acquisition and analysis unit 19 transmits information, which specifies the image for references, and related information acquired in step S31a to the shared object generating unit 21 (step S36a). In addition, when it is determined that the image for references cannot be generated in step S33a, the information acquisition and analysis unit 19 transmits the related information acquired in step S31a to the shared object generating unit 21. The explanation on the processing A and the processing B is thus completed.

<Processing C for Acquiring Specific Information of Past Study and Series Related to a Corresponding Study>

Figure 6:
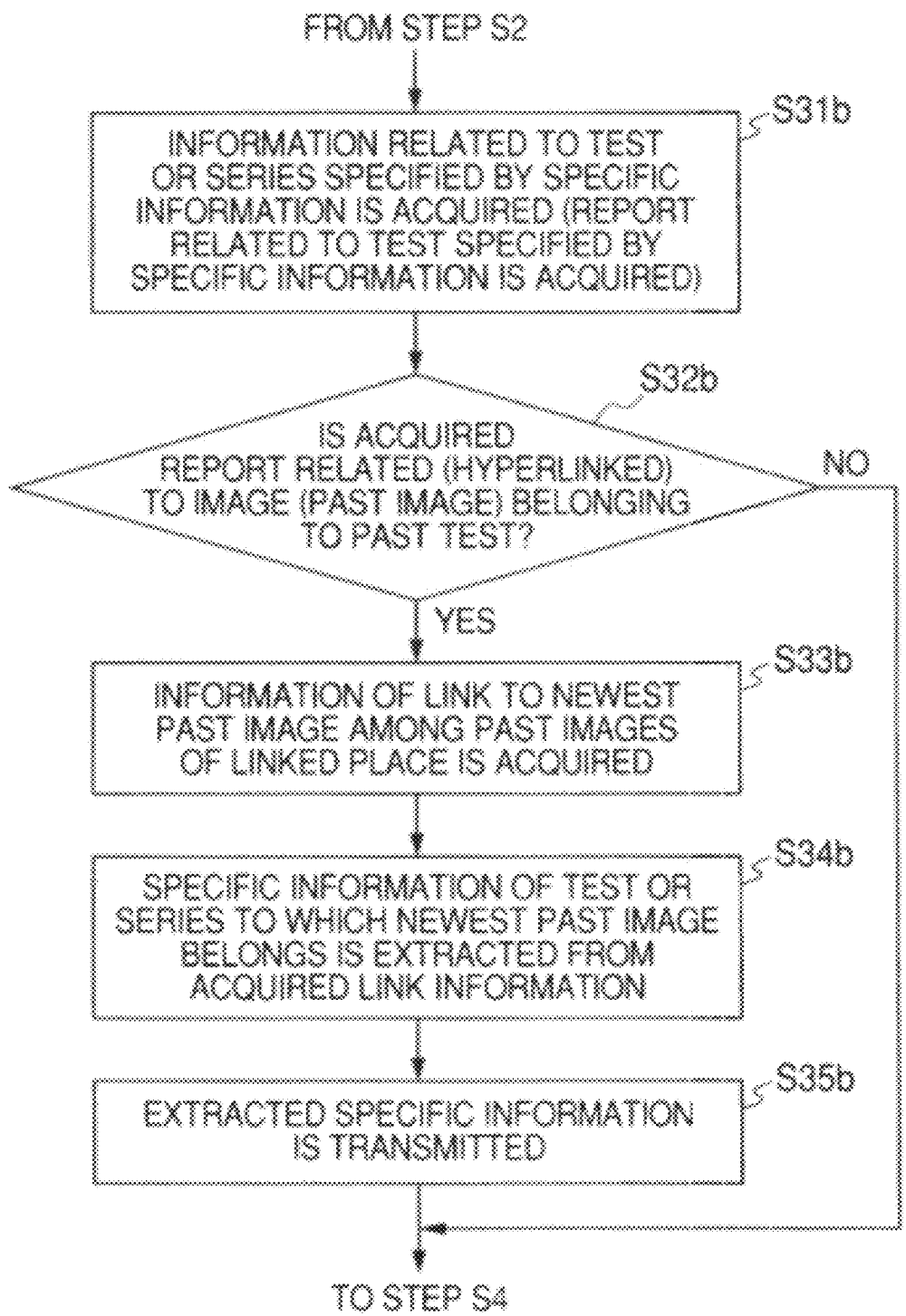
FIG. 6 is a flow chart illustrating processing for acquiring link information on a past image from a report storage unit, which is executed in step S3 shown in FIG. 3.

Next, processing for specifying a past study related to a corresponding study and acquiring specific information from a report stored in the report storage unit 13, which is executed by the information acquisition and analysis unit 19 in step S3, will be described. FIG. 6 is a flow chart illustrating processing for acquiring link information. As shown in FIG. 6, the information acquisition and analysis unit 19 accesses the report storage unit 13 (or report preparation support apparatus designated beforehand) by referring to the storage place table and acquires a report of a corresponding study by using a patient ID, a study date, modality, an accession number, and the like (step S31b).

Then, the information acquisition and analysis unit 19 analyzes the content of the acquired report and determines whether or not the corresponding report is hyperlinked to a past image (step S32a).

When it is determined that the corresponding report is not hyperlinked to the past image in step S32b (step S32b: NO), the information acquisition and analysis unit 19 ends the processing for acquiring link information.

When it is determined that the corresponding report is hyperlinked to the past image in step S32b (step S32b: YES), the information acquisition and analysis unit 19 acquires link information on a latest past image among past images of a linked place associated by the hyperlink (step S33b). Specifically, the link information includes specific information of a study or series to which an image belongs. After the link information is acquired, the information acquisition and analysis unit 19 extracts specific information, such as a study UID or a series UID, from the acquired link information (step S34b). The acquired specific information is specific information for specifying a study or series to which a latest past image belongs. Then, the information acquisition and analysis unit 19 transmits the extracted specific information as related information to the shared object generating unit 21 (step S35b). The explanation on the processing C is thus completed.

In addition, both the <processing A & processing B> and the <Processing C> may be performed or either one of the <processing A & processing B> and the <Processing C> may be performed. This selection may be arbitrarily set through the operation unit 23 by a user.

[Generation of a Shared Object: Step S4]

As shown in FIG. 3, the shared object generating unit 21 generates a shared object for every corresponding series or series belonging to a corresponding study, for example, on the basis of related information received from the information acquisition and analysis unit 19.

Figure 7:
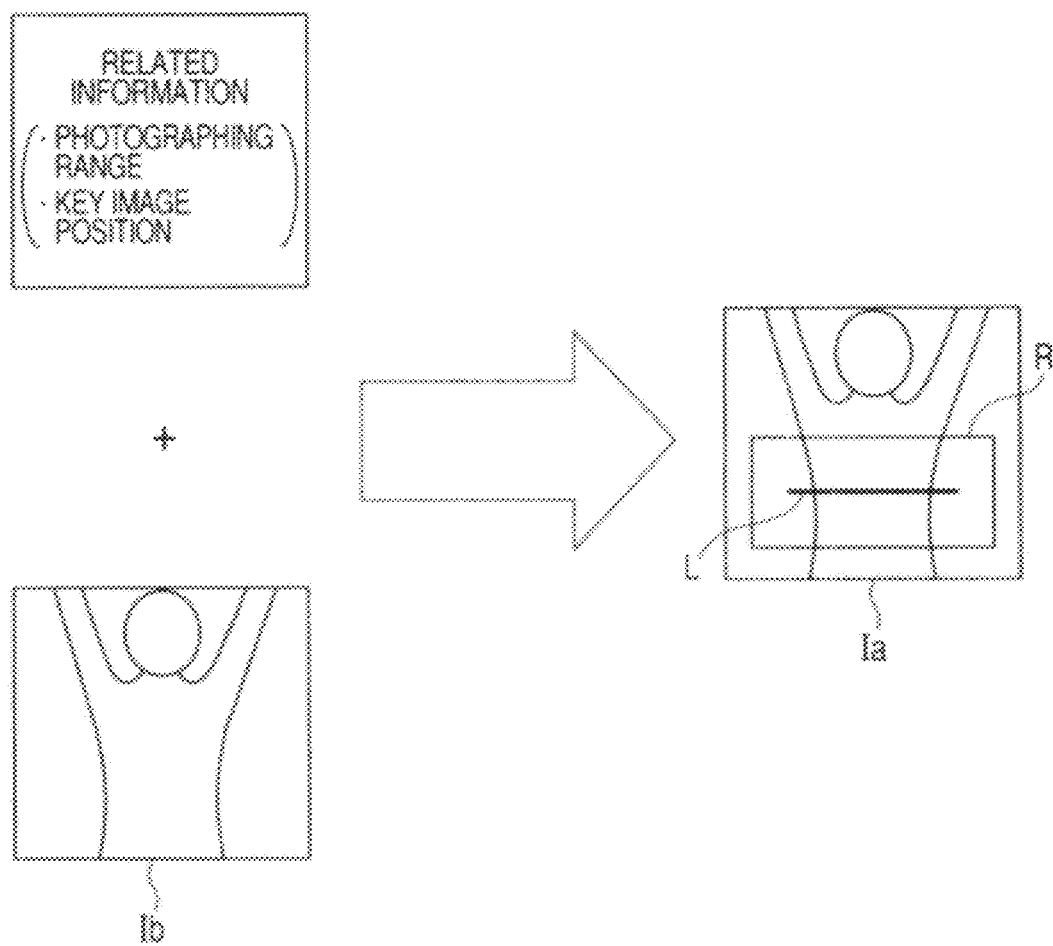
FIG. 7 is a view for explaining the concept of a reference image generated to include an image for references, a scan range or a key image position, and the like by the shared object generating unit shown in FIG. 1.

FIG. 7 is a view for explaining the concept of a shared object. First, the shared object generating unit 21 acquires actual data of an image Ib for references on the basis of information for specifying the image Ib for references which is the related information. Then, the shared object generating unit 21 generates a reference image Ia by drawing a scan range R and a key image position L on the acquired image Ib for references.

This drawing is performed by overlay or a technique of performing direct drawing on a pixel, for example.

In addition, the shared object generating unit 21 generates a shared object by generating DICOM additional information including link information, a scan condition, an image generation condition, and the like using the related information received from the information acquisition and analysis unit 19.

In addition, such generation of a shared object is repeatedly executed in the unit of series or a study.

[Storage of a Shared Object: Step S5]

The generated shared object is stored, as a new DICOM object related to a corresponding study or series, in the image storage unit 11. In addition, a storage place of the shared object is registered in the storage place table included in the data management unit 15. After registration, a notice of completion of processing is displayed on a display unit, for example, and a series of generation processing are completed.

(Effects)

According to the configuration described above, the following effects can be obtained.

The medical image storage apparatus 1 acquires related information related to the corresponding study or series from the image data acquired in a past study or series, additional information thereof, and additional information such as a report on the basis of specific information of a study or series for which a shared object is to be generated. The medical image storage apparatus 1 analyzes the image type, the image direction, the image position, a scan range, and the like included in the acquired related information and selects an image for references from image data related to the corresponding study or series. By drawing a scan range, a key image, and the like on the selected image for references, the medical image storage apparatus 1 acquires a reference image. The medical image storage apparatus 1 can generate a shared object for the corresponding study or series in the unit of series, for example, by using the acquired related information and the reference image. Therefore, the medical image storage apparatus 1 can generate a shared object afterwards even for a study executed before a system using a shared object is introduced. By using the shared object generated afterwards, it becomes possible to reproduce a past study or series with high precision, for example, in a case of performing image diagnosis of the postoperative progress or observing a temporal change of a tumor. In addition, since it is not necessary to perform a work, such as referring and checking an interpretation report in a previous study, a work flow in the department of radiology is improved.

Moreover, in the case when an image for references is not present, the medical image storage apparatus 1 generates a proper MPR image, for example, from existing image data and generates a reference image included in the shared object by using the generated MPR image as an image for references. Accordingly, the medical image storage apparatus 1 can generate a shared object including a reference image afterwards even in the case when the image for references is not present. As a result, the medical image storage apparatus 1 can generate shared objects related to all studies or series afterwards. Thus, the medical image storage apparatus 1 can contribute to improvement in the work efficiency of image diagnosis, improvement in reproducibility of past image diagnosis, and the like.

Furthermore, the medical image storage apparatus 1 can acquire link information on a past image, which is present in a corresponding report, from a report related to a corresponding shared object and make the acquired link information included in the shared object. As a result, the medical image storage apparatus 1 can generate the relationship with a past image in the shared object even in the case when the shared object is generated afterwards.

Second Embodiment

In general, in management of image data based on the DICOM standard, information defined in standard DICOM standard is not enough for a scan condition. For this reason, in the case of information that runs short, information is held as a private tag.

However, since the private tag portion is information unique to an apparatus, it is generally difficult to generate the private tag portion afterwards.

A medical image storage apparatus 1 according to a second embodiment makes a shared object, which is generated afterwards, richer in content by specifying a past study or series similar to a study or series, for which a shared object needs to be generated afterwards, and using information included in a shared object corresponding to the specified study or series.

Figure 8:
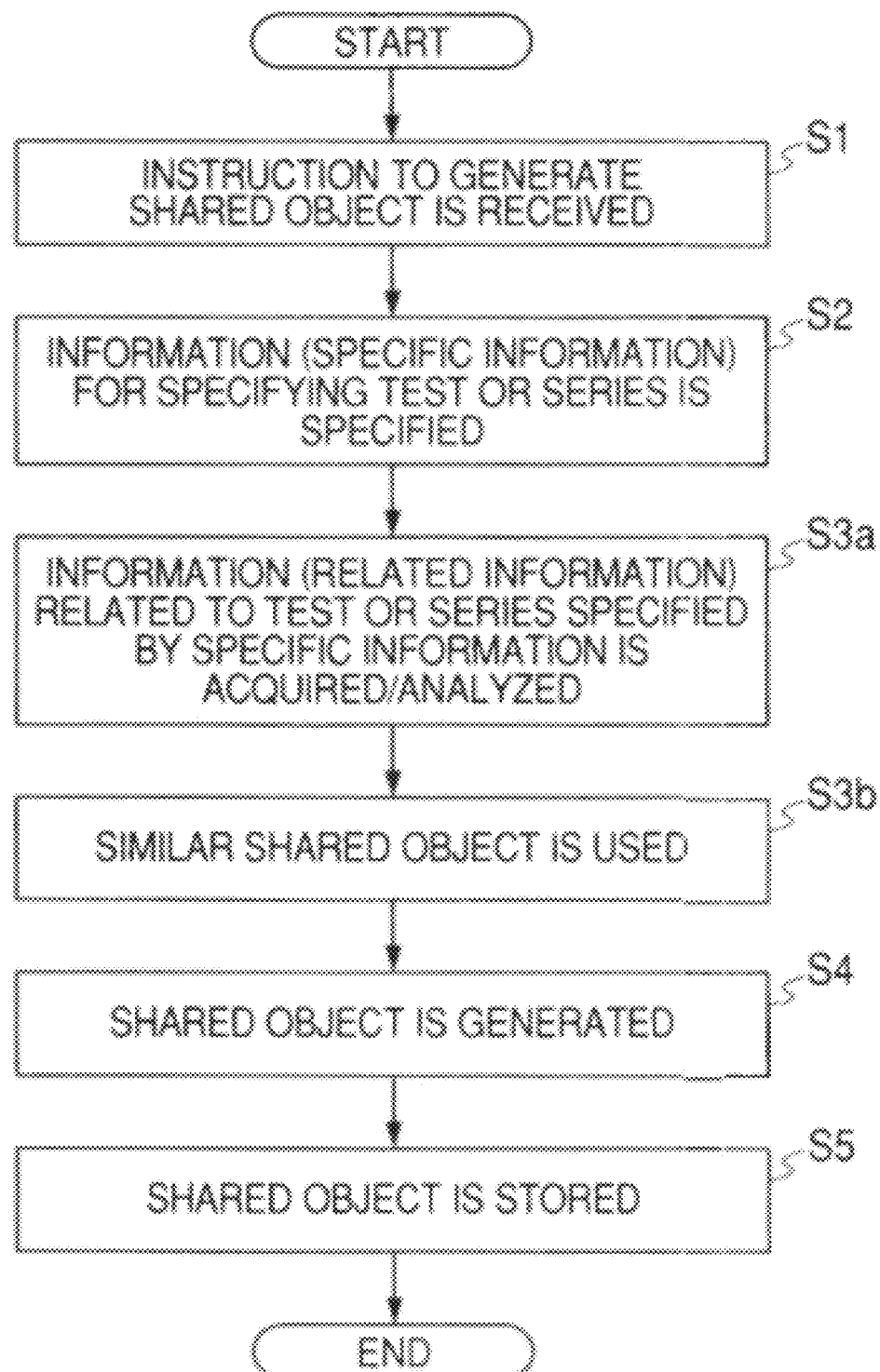
FIG. 8 is a flow chart illustrating image diagnosis support processing in a second embodiment of the invention, which is executed under the control of the control unit shown in FIG. 1.

FIG. 8 is a flow chart illustrating image diagnosis support processing executed under the control of a control unit 17 in the second embodiment. As shown in FIG. 8, in the image diagnosis support processing according to the second embodiment, processing (step S3b) for using a similar shared object is added.

Figure 9:
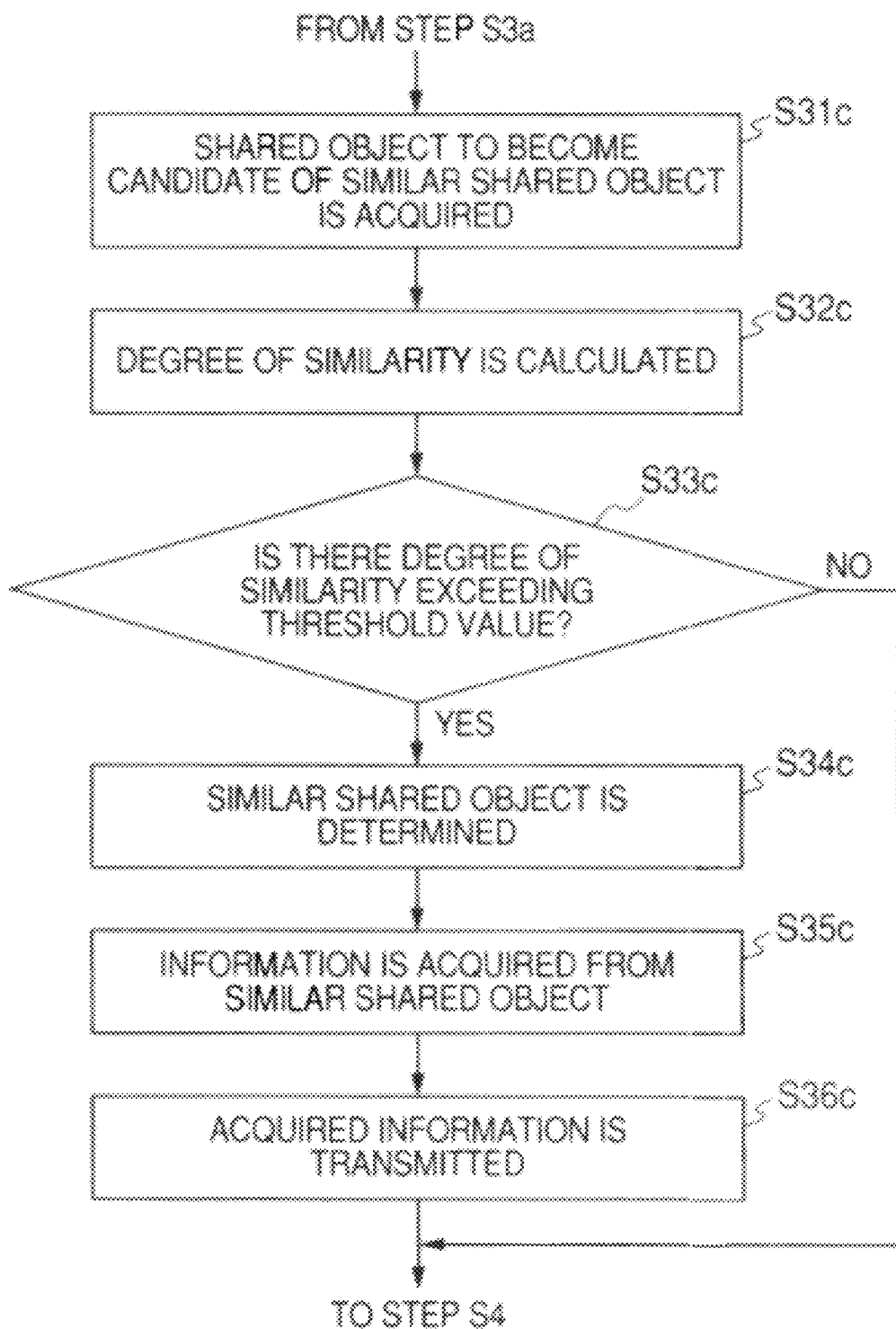
FIG. 9 is a flow chart illustrating processing for using a similar shared object in the second embodiment of the invention, which is executed in step S3b of FIG. 8.

FIG. 9 is a flow chart illustrating processing executed by an information acquisition and analysis unit 19 in step S3b of FIG. 8. As shown in FIG. 9, the information acquisition and analysis unit 19 first acquires a shared object to become a candidate of a similar shared object (step S31c). Since acquisition of the shared object to become a candidate is performed to supplement information (that is, private tag portion) unique to an apparatus, the acquisition of the shared object is executed with respect to the image storage unit 11 by using a station name or a scanned portion of DICOM additional information of a study for which a shared object needs to be generated afterwards. Either one shared object or a plurality of shared objects may be acquired in step S31c.

Then, the information acquisition and analysis unit 19 calculates the degree of similarity of the acquired shared objects (step S32c). That is, the information acquisition and analysis unit 19 calculates the degree of similarity while referring to a similarity decision table shown in FIG. 10, for example. FIG. 10 is a view illustrating an example of a similarity decision table. For example, the information acquisition and analysis unit 19 compares a value of an item 'tube voltage', which is included in a shared object A to be generated, with a value of an item 'tube voltage' included in an acquired shared object B. If the values are equal, the information acquisition and analysis unit 19 adds five points to the degree of similarity of the shared object A. If the values are not equal, the information acquisition and analysis unit 19 does not add a point. In this way, the degree of similarity is calculated by comparing values of all items included in the shared object A. In other words, the degree of similarity of the shared object A is the sum of addition weights assigned to all items of the shared object A having the same values as values of the items included in the shared object B.

After the degree of similarity is calculated, the information acquisition and analysis unit 19 determines whether or not any of the calculated degrees of similarity exceeds a predetermined threshold value (step S33c).

When it is determined that there is no degree of similarity exceeding the predetermined threshold value (step S33c: NO), the information acquisition and analysis unit 19 ends the processing for using a similar shared object and proceeds to step S4.

When it is determined that there is a degree of similarity exceeding the predetermined threshold value (step S33c: YES), the information acquisition and analysis unit 19 determines a shared object, which has a largest degree of similarity, among shared objects acquired in step S31c as a similar shared object (step S34c). Then, the information acquisition and analysis unit 19 acquires information (that is, additional information including a reference image and a private tag portion) included in the similar shared object (step S35c). Then, the information acquisition and analysis unit 19 transmits the information acquired in step S35c to the shared object generating unit 21 (step S36c).

According to the configuration described above, the medical image storage apparatus 1 can use information (in particular, information on a private tag portion) included in a shared object having highest similarity in the case of generating a shared object afterwards. As a result, since the medical image storage apparatus 1 can include information unique to an apparatus, a shared object including information sufficient for reproducing a past study or series can be generated afterwards.

Third Embodiment

For example, the shared object acquired in step S31c in the second embodiment may include information (for example, UID of another shared object, information indicating the location, or link information) for specifying another shared object to be referred instead of including actual data (or information for specifying actual data) regarding a scan condition, a reference image, and the like. In this case, a medical image storage apparatus 1 according to a third embodiment makes a shared object, which is generated afterwards, richer in content by accessing another shared object to be referred and using information included in the accessed shared object. In addition, another shared object to be referred is hereinafter called an alternative shared object.

Since the image diagnosis support processing executed under the control of a control unit 17 in the third embodiment is the same as that shown in FIG. 8, an explanation thereof is omitted. FIG. 11 is a flow chart illustrating processing for using an alternative shared object, which is executed by an information acquisition and analysis unit 19 in step S3b of FIG. 8. As shown in FIG. 11, the information acquisition and analysis unit 19 first acquires a shared object to become a candidate of a similar shared object (step S31d). Processing in step S31d is the same as that in step S31c of the processing for using a similar shared object in the second embodiment. Then, the information acquisition and analysis unit 19 determines whether or not specific information of an alternative shared object is included in the acquired shared object (step S32d).

When it is determined that the specific information of the alternative shared object is not included (step S32d: NO), the information acquisition and analysis unit 19 proceeds to step S4.

When it is determined that the specific information of the alternative shared object is included (step S32d: YES), the information acquisition and analysis unit 19 accesses the alternative shared object and acquires information included in the accessed alternative shared object (step S33d). Then, the information acquisition and analysis unit 19 transmits the acquired information to the shared object generating unit 21 (step S34d).

Moreover, in the case when specific information of other shared objects to be further referred is included in the shared object accessed in step S33d, it may be possible to access the other shared objects as needed. It is preferable to be able to arbitrarily set how far the other shared objects are traced back by using a predetermined I/F provided in the operation unit 23, for example.

According to the configuration described above, even when specific information of an alternative shared object is stored in another shared object to be referred instead of actual data regarding a scan condition, a reference image, and the like being stored, the medical image storage apparatus 1 can trace back to a shared object from which required information can be acquired. As a result, the medical image storage apparatus 1 can generate a shared object, which includes information sufficient for reproducing a past study or series, afterwards.

In addition, the invention is not limited to the embodiments described above but may be embodied in practice by modifying constituent components without departing from the scope and spirit of the invention. For example, specific modifications include the following examples.

Each of the functions in the first to third embodiments of the invention may be realized by installing a program, which is used to execute corresponding processing, in a computer, such as a workstation, and by loading the program into a memory. At this time, a program capable of causing a computer to execute a corresponding technique may be distributed in a state where the program is stored in a recording medium, such as a magnetic disk (for example, a floppy (registered trademark) disk or a hard disk), an optical disk (for example, a CD-ROM or a DVD), and a semiconductor memory.

In addition, various kinds of inventions may be realized by proper combination of the plurality of constituent components disclosed in the embodiments described above. For example, some constituent components may be eliminated from all components shown in the above embodiments. Moreover, constituent components in different embodiments may be appropriately combined.

In this manner, according to the first to third embodiments described above, it is possible to realize an image diagnosis support system and an image diagnosis support method capable of generating a shared object afterwards even for a study or series executed before a system that uses a shared object is introduced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image diagnosis support system comprising:
   a specifying unit that specifies specific information for specifying a specific study or series for object data to be generated, the object data being obtained by adding at least one information of a scan condition, a scan range, and a key image position as a basis of a diagnosis in a reference image;
   a first determination unit that determines whether or not a specific image for generating the reference image is present in the specific study or series on the basis of additional information of at least one image related to the specific study or series; and
   a first generation unit that generates the object data by using the specific image and at least one information of a scan condition, a scan range, and a key image position of the additional information when it is determined that the specific image is present.

2. The image diagnosis support system according to claim 1,
   wherein the additional information further includes at least one of an image position, an image direction, an image type, a study UID, a series UID, a study instance UID, and a series instance UID in addition to the scan condition, the scan range, and the key image position.

3. The image diagnosis support system according to claim 1, further comprising:
   a second generation unit that generates the specific image by using at least one information of the scan condition, the scan range, and the key image position of the additional information and at least one image related to the specific study or series when it is determined that the specific image is not present.

4. The image diagnosis support system according to claim 1, further comprising:
   a first acquisition unit that acquires information included in object data about a study or series similar to the specific study or series on the basis of the specific information,
   wherein the first generation unit generates object data about the specific study or series by using the acquired information.

5. The image diagnosis support system according to claim 4,
   wherein when information on other object data to be referred is included in the acquired information, the first acquisition unit acquires the information included in the other object data.

6. The image diagnosis support system according to claim 1, further comprising:
   a second acquisition unit that acquires a report related to the specific study or series; and
   a second determination unit that determines whether or not link information, which indicates a storage place of an image related to other studies or series different from the specific study or series, is included in the acquired report,
   wherein the first generation unit causes information, which specifies an image related to the other studies or series, extracted from the link information to be further included when it is determined that the link information is present.

7. The image diagnosis support system according to claim 1,
   wherein the reference image is an image for indicating at least one of the scan range in the specific study or series and the key image position.

8. An image diagnosis support system comprising:
a specifying unit that specifies specific information for specifying a medical image including a plurality of images;
a first determination unit that determines whether or not a specific image for generating a reference image is present, the specific image being related to the medical image specified by the specific information; and
a first generation unit that generates object data by using the specific image and information related to the medical image specified by the specific information when it is determined that the specific image is present, the information including at least one of a scan condition, a scan range, and a position of a key image used as a basis of a diagnosis.

9. The image diagnosis support system according to claim 8,
wherein the specific information is a study UID or a series UID specified by DICOM.

10. The image diagnosis support system according to claim 8,
wherein the first determination unit determines whether or not the specific image is included in the specified medical image or whether or not the specific image related to the specified medical image is present.

11. The image diagnosis support system according to claim 8, further comprising:
a second generation unit that generates the specific image on the basis of the specified medical image when it is determined that the specific image is not present.

12. The image diagnosis support system according to claim 8, further comprising:
an acquisition unit that acquires a report related to the specified medical image; and
a second determination unit that determines whether or not link information, which indicates a storage place of an image related to a medical image different from the specific medical image, is included in the acquired report,
wherein the generation unit causes information, which specifies the related image extracted from the link information, to be further included in the object when it is determined that the link information is present.

13. An image diagnosis support system comprising:
a specifying unit that specifies specific information for specifying a specific study or series for which object data to be generated, the object data being obtained by adding at least one information of a scan condition, a scan range, and key image position as a basis of a diagnosis in an image;
an acquisition unit that acquires a report related to the specific study or series;
a determination unit that determines whether or not link information is included in the acquired report, the link information indicating a storage place of an image related to other studies or series different from the specific study or series; and
a generation unit that generates the object data by using first information and second information when it is determined that the link information is present, the first information being extracted from the link information and for specifying an image related to the other studies or series, the second information including at least one information of a scan condition, a scan range, and a key image position of additional information of at least one image related to the specific study or series.

14. An image diagnosis support method comprising:
specifying a specific study or series for object data to be generated, the object data being obtained by adding at least one information of a scan condition, a scan range, and a key image position as a basis of a diagnosis in a reference image;
determining whether or not a specific image for generating the reference image is present in the specific study or series on the basis of additional information of at least one image related to the specified specific study or series; and
generating the object data by using the specific image and at least one information of a scan condition, a scan range, and a key image position of the additional information when it is determined that the specific image is present.

15. An image diagnosis support method comprising:
specifying specific information for specifying a medical image including a plurality of images;
determining whether or not a specific image for generating a reference image is present, the specific image being related to the medical image specified by the specific information; and
generating object data by using the specific image and information related to the medical image specified by the specific information when it is determined that the specific image is present, the information including at least one of a scan condition, a scan range, and a position of a key image used as a basis of a diagnosis.

16. An image diagnosis support system comprising:
a specifying unit that specifies information identifying a first study or series for which object data is to be generated;
a first determination unit that determines whether or not an image, available as a reference image, is present in the first study or series on the basis of additional information of one or more images of the first study or series;
a first generation unit that generates the object data using the image and at least one information of a scan condition, a scan range, and a key image position when it is determined that the image is present in the first study or series, the information of the scan condition, the scan range, and the key image position being a basis of a diagnosis in the reference image; and
a first storing unit that stores the object data such that the object data is linked to the first study or series.

* * * * *